United States Patent [19]

Woodward et al.

[11] Patent Number: 5,637,617
[45] Date of Patent: Jun. 10, 1997

[54] METHODS FOR USE OF $GABA_A$ RECEPTOR GABAERGIC COMPOUNDS

[75] Inventors: Richard M. Woodward, Aliso Viejo; Ricardo Miledi, Irving, both of Calif.

[73] Assignee: The Regents of the University of California, Oakland, Calif.

[21] Appl. No.: 221,883

[22] Filed: Apr. 1, 1994

[51] Int. Cl.$^6$ .................................................. A61K 31/19
[52] U.S. Cl. ........................................ 514/567; 514/568
[58] Field of Search ................................ 514/567, 568

[56] References Cited

PUBLICATIONS

Picrate and Niflumate Block Anion Modulation of Radioligand Binding to the β–Aminobutyric Acid/Benzodiazepine Receptor Complex Evoniuk and Skolnick, *Molecular Pharmacology*, 34:837–842, 1988.

Chloride Transport Blockers Prevent N–Methyl–D–aspartate Receptor–Channel Complex Activation Lerma and Del Rio, *Molecular Pharmacology*, 41:217–222, 1991.

Actions of Pentobarbital on Rat Brain Receptors Expressed in Xenopus Oocytes Parker, *The Journal of Neuroscience*, No. 6, 8:2290–2297, Aug. 1986.

Inhibition of Anion Permeability by Amphiphilic Compounds in Human Red Cell: Evidence for an Interaction of Niflumic Acid with the Band 3 Protein Cousin and Motais, *J. Membrane Biol.*, 46:125–153, 1979.

Gastritis, Duodenitis, and Bleeding Duodenal Ulcer Following Mefenamic Acid Therapy Wolfe, et al., *Arch. Intern Med.*, 136:923–925, Aug. 1976.

The Actions of the Non–Steroidal Anti–Inflammatory Drug, Metenamic Acid with the $GABA_A$ Receptor Halliwell et al., *Br. J. Pharmacol.*, 96:139P, 1989.

Non–competitive inhibition of $GABA_A$ responses by a new class of quinolones and non–steroidal anti–inflammatories in dissociated frog sensory neurones Yakushiji, et al., *Br. J. Pharmacol.*, 105:13–18, 1992.

Interaction of various non–steroidal anti–inflammatories and quinolone antimicrobials on GABA response in rat dissociated hippocampal pyramidal neurons Shirasaki, et al., *Brain Research*, 562:329–331, 1991.

Inhibition of $GABA_A$ Receptor–Mediated Current Responses By Enoxacin (New Quinolone) and Felbinac (Non–Steroidal Anti–Inflammatory Drug) In . . . Kawakami, et al., *Biol. Pharm. Bull.*, No. 7, 16:726–728, 1993.

Responses to GABA, glycine and β–alanine induced in Xenopus oocytes by messenger RNA from chick and rat brain Parker, et al., *Proc. R. Soc. Lond. B.*, 233:201–216, 1988.

Activation of protein kinase C differentially modulates neuronal $Na^+$, $Ca^{2+}$, and βaminobutyrate type A channels Sigel and Baur, *Proc. Natl. Acad. Sci. USA*, 85:6192–6196, Aug. 1988.

Effects of Fenamates and Other Nonsteroidal Anti–inflammatory Drugs on Rat Brain $GABA_A$ Receptors Expressed in Xenopus Oocytes Woodward, et al., *The Jrnl. of Pharm. and Exp. Ther.*, 268:806–817, 1994.

*Primary Examiner*—Phyllis G. Spivack
*Attorney, Agent, or Firm*—Fish & Richardson P.C.

[57] ABSTRACT

A method is disclosed for potentiating mammalian $GABA_A$ receptor responses to GABA. The receptor responses are potentiated according to the invention by contacting $GABA_A$ receptors with GABA and an effective amount of non–steroidal anti-inflammatory agents, in particular, fenamates and structurally related compounds.

7 Claims, 10 Drawing Sheets

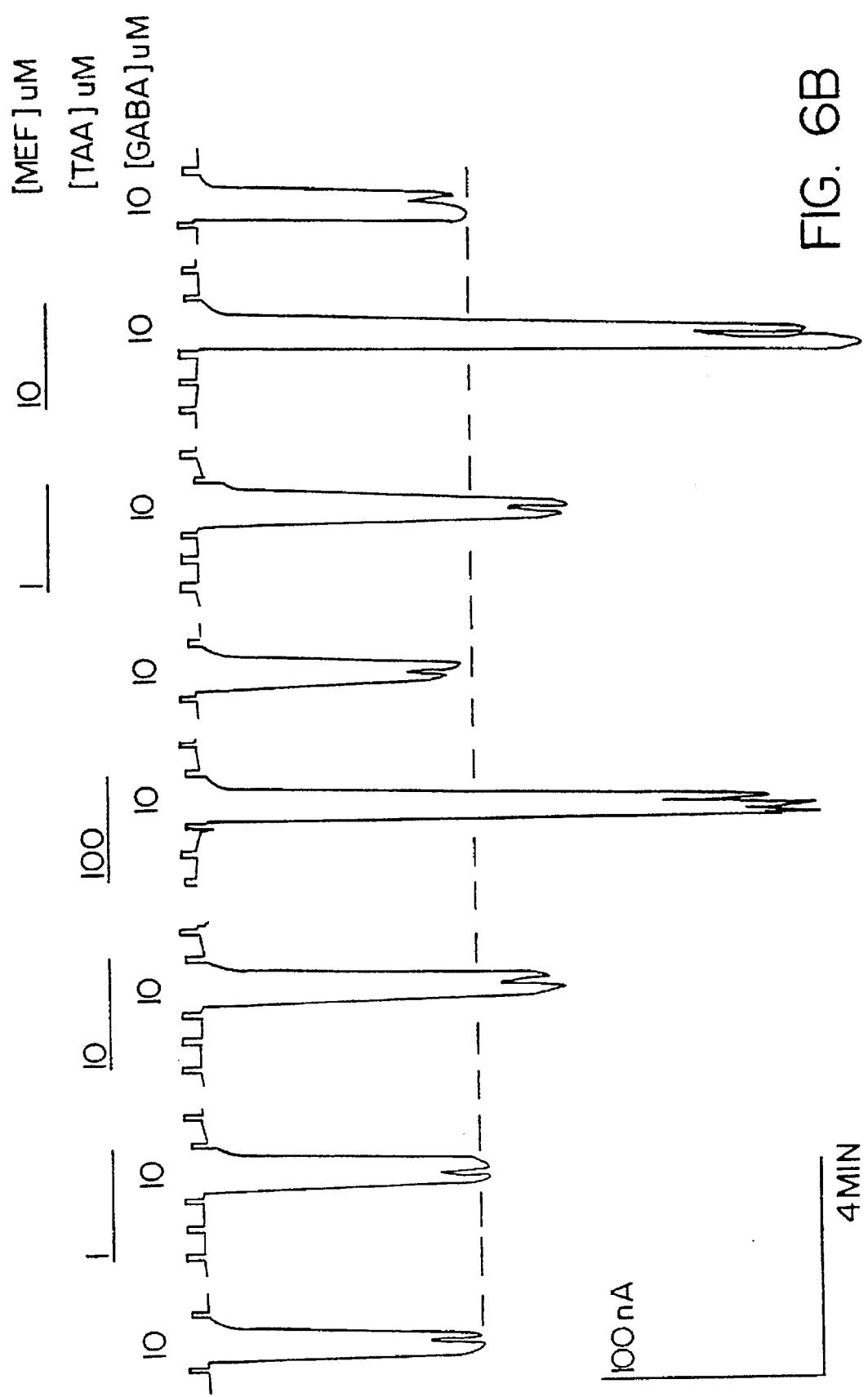

METHODS FOR USE OF GABA$_A$ RECEPTOR GABAERGIC COMPOUNDS

BACKGROUND OF THE INVENTION

1. Field of the Invention

This invention relates to methods for the use of compounds to potentiate the effects of gamma-aminobutyric acid (GABA) in mammalian tissues which contain receptors which will bind GABA. In particular, the invention relates to the use of certain non-steroidal agents which enhance the response of GABA$_A$ receptors to GABA and are, therefore, useful as GABAergic agents.

2. History of the Prior Art.

Gamma-aminobutyric acid, commonly known as GABA, is an amino acid which serves as one of the major neurotransmitters in the mammalian central nervous system, particularly the brain.

In general, neurotransmitters are responsible for regulating the conductance of ions across neuronal membranes. At rest, the neuronal membrane possesses a potential or membrane voltage of approximately −80 mv, the interior being negative with respect to the exterior of the cell. The potential is the result of ion balance (e.g., $K^+$, $Na^+$, $Cl^-$, organic anions) across the neuronal membrane, which is semipermeable. Neurotransmitters are stored in presynaptic vesicles and are released under the influence of neuronal action potentials. When released into the synaptic cleft, an excitatory chemical transmitter such as acetylcholine will cause membrane depolarization (a decrease from its resting value of −80 mv). This effect is mediated by post-synaptic hetero-oligomeric proteins—nicotinic receptors—which are stimulated by acetylcholine to increase membrane permeability to $Na^+$ and $Ca^{2+}$ ions. The reduced membrane potential stimulates neuronal excitability and results in the generation of a post-synaptic action potential, which may cause excitation or inhibition in other nerve cells.

The profound influence of GABA on the central nervous system is related to the presence of GABA receptors in up to 40% of the neurons in the brain alone. GABA regulates the excitability of individual neurons by regulating the conductance of ions across the neuronal membrane. For example, GABA interacts with its recognition site on GABA$_A$ receptors, resulting in an increase in membrane permeability to chloride ions that renders the neuron less susceptible to further stimulation. Thus, GABA receptors have been implicated in the mediation of mental depression, anxiety, seizures and responses to other stresses on the central nervous system.

Flufenamic acid, meclofenamic acid, mefenamic acid, and niflumic acid are all derivatives of N-phenyl-anthranilic acid which are commonly referred to as "fenamates". Fenamates have been used in Europe and Japan as non-steroidal anti-inflammatory agents ("NSAIDs"), but have not been used widely in the United States because of a relatively high incidence of gastrointestinal side effects observed in clinical trials (see, e.g., Wolfe, et al., *Arch. Intern. Med.*, 136:923–925, 1976).

At the molecular level, the fenamates are known to inhibit anion transport through certain ion channels. For example, mefenamic acid has been shown to inhibit current responses to GABA in disassociated rat neuronal cells (Shirasaki, et al., *Brain Res.*, 562:329–331, 1991). Niflumic acid has been shown to be a fairly potent inhibitor of anion transport in erythrocytes (Cousin, et al., *J. Membr. Biol.* 46:125–153, 1979). In cultured spinal cord neurons, niflumic and flufenamic acids inhibit the responses of N-methyl-D aspartate receptors to their ligand (Lerma, et al., *Mol. Pharmacol.*, 41:217–22, 1992) and also inhibit $Ca^{2+}$ activated $Cl^-$ channels in the oocytes of the frog *Xenopus laevis*.

The observations concerning the effect of fenamates on *Xenopus laevis* oocytes are of interest because *Xenopus* oocytes are used extensively as an expression system for mammalian neurotransmitter receptors and ion channels, including those which interact with GABA. Generally, the products of the Xenopus oocyte expression system are structurally and functionally like their corresponding native receptor or ion channel in most respects. For example, poly (A)$^+$ RNA isolated from rat cerebral cortex or chick optic lobe expresses GABA$_A$ receptor subunits that assemble to form GABA-activated $Cl^-$ channels. The expressed receptors generally respond to ligands which are known to be potentiatory or inhibitory agents for GABA receptors in the same manner as the native receptors (see, e.g., Parker, et al., *J. Neuroscience*, 6:2290–2297, 1986; Parker, et al., *Proc. R. Soc. Land. B.*, 233:201–216, 1988; Woodward, et al., *Mol. Pharmacol.*, 41:89–103, 41:1107–115, and 42:165–173 (all 1992); and Sigel, et al., *Proc. Nat'l. Acad. Sci.*, USA, 85:6192–6196, 1988).

SUMMARY OF THE INVENTION

Using *Xenopus laevis* oocytes as a model, it has now been found that certain NSAIDs, and related analogs thereof, effectively modulate GABA$_A$ receptors by potentiating GABA responses and/or inhibiting maximum responses (i.e., the "GABAergic activity" of the compound).

GABAergic activity is observed with compounds of formula (I):

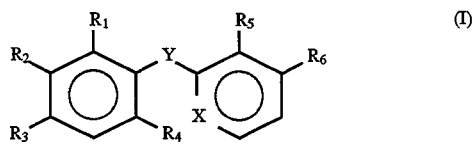

wherein X is C or N; Y is NH or no bond; $R_1$ is H, halogen or $CH_3$; $R_2$ is H, $CH_3$, $CF_3$ or $NO_2$; $R_3$ is H, halogen, $CH_3$ or $CF_3$; $R_4$ is H, halogen, $CH_3$ or $CF_3$; $R_5$ is H or COOH; $R_6$ is H or COOH; and $R_7$ is H or OH, with the proviso that either $R_5$ or $R_6$ will always be COOH or COOCH$_2$.

As used herein, the term "halogen" preferably means chlorine or fluorine, but may also mean bromine or iodine.

Also useful in this invention are pharmaceutically acceptable salts of compounds of formula (I).

Further included in this invention are in vivo hydrolyzable esters of compounds of formula (I).

The invention still further concerns a pharmaceutical composition comprising a GABAergic amount of a compound of formula (I) in a pharmaceutically acceptable carrier.

The invention also provides a method for modulating the response of GABA$_A$ receptors to GABA, which comprises contacting cells or tissue containing GABA$_A$ receptors with a GABAergic amount of a compound of formula (I) or a pharmaceutically-acceptable salt thereof or a pharmaceutical composition thereof.

BRIEF DESCRIPTION OF THE DRAWINGS

FIG. 1 (A) and (B) show data from the same oocyte.

DETAILED DESCRIPTION OF THE INVENTION

GABAergic Compounds of the Invention

Figure 1A:
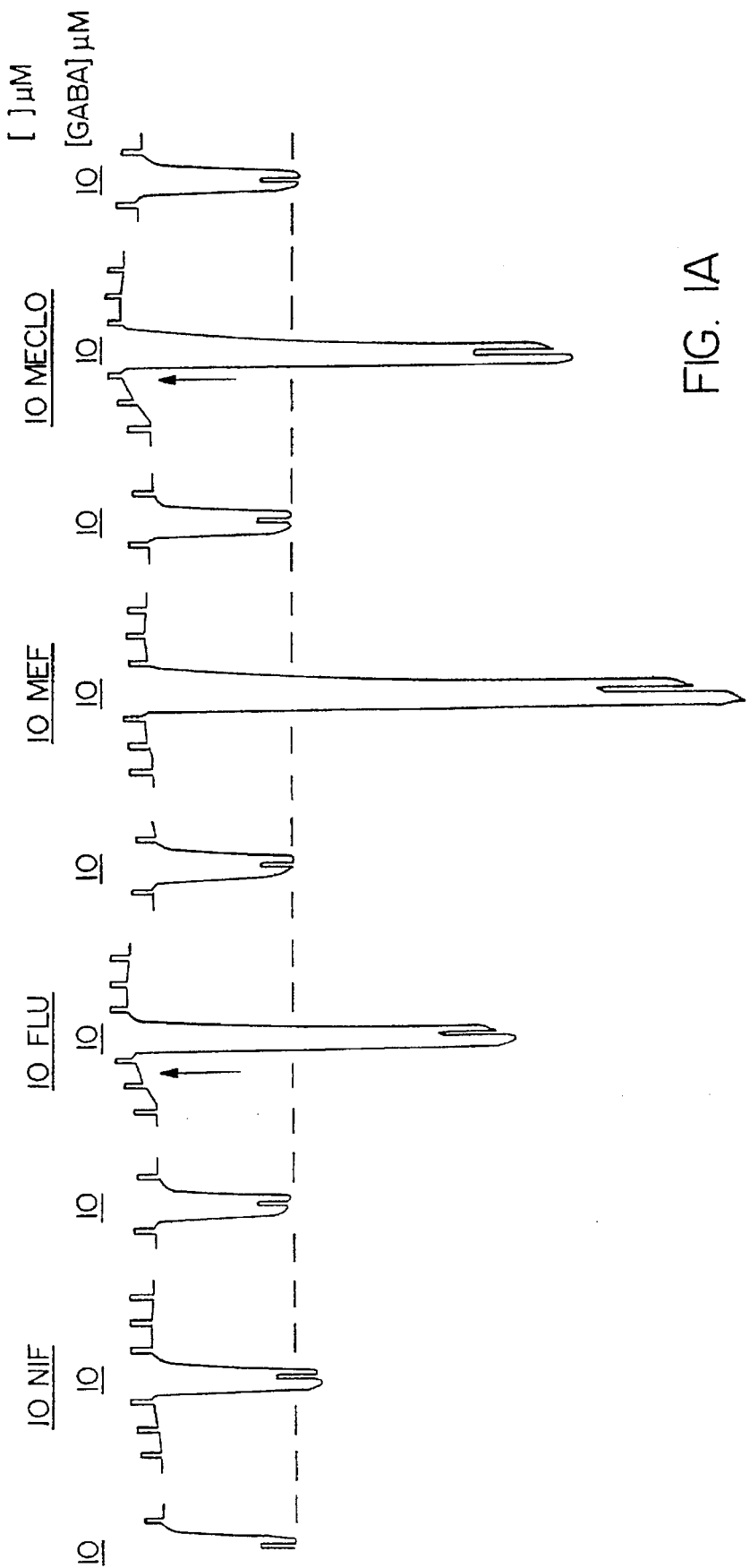
FIG. 1 (A–B) demonstrates the GABA$_A$ potentiating capacity of the GABAergic compounds of the invention. The records were separated by 5–20 minutes, depending on the level of potentiation.

A majority of the compounds encompassed by the formula (I) are known non-steroidal anti-inflammatory agents ("NSAIDs"). A first preferred group of compounds of this invention are those wherein X is C and Y is no bond. Especially favored within this group is the compound wherein $R_1$ $R_2$, and $R_5$ are hydrogen; $R_3$ and $R_4$ are both fluorine; $R_6$ is COOH; and $R_7$ is OH. This particular compound is known as diflunisal (see, "The Merck Index", 11th ed., monograph no. 3130).

A second preferred group of compounds of this invention are those wherein Y is NH. Especially favored within this group are those wherein $R_3$ is H, $R_5$ is COOH, and $R_6$ and $R_7$ are both H.

Preferred individual compounds are:

Flufenamic acid (compound of formula (I) wherein $R_1$ is H, $R_2$ is $CF_3$, $R_4$ is H, Cl, and X is C) (see, "The Merck Index", 10th ed., monograph no. 4038).

Meclofenamic acid (compound of formula (I) wherein $R_1$ is Cl, $R_2$ is $CH_3$, $R_4$ is Cl, and X is C) (see, "The Merck Index", 11th ed., monograph no. 5659);

Mefenamic acid (compound of formula (I) wherein $R_1$ and $R_2$ are both $CH_3$, $R_4$ is H, and X is C) (see, "The Merck Index", 11th ed., monograph no. 5680);

Niflumic acid (compound of formula (I) wherein $R_1$ is H, $R_2$ is $CF_3$, $R_4$ is H, and X is N) (see, "The Merck Index", 11th ed., monograph no. 6444);

N-phenyl-anthranilic acid ("PAA") (compound of formula (I) wherein $R_1$, $R_2$, and $R_4$ are each H, and X is C) (see, "The Merck Index", 11th ed., monograph no. 7944);

N-(O-tolyl) anthranilic acid ("TAA") (compound of formula (I) wherein $R_1$ is $CH_3$, $R_2$, and $R_4$ are both H, and X is C) (see, "The Merck Index", 10th ed., monograph no. 7152);

N-(3-nitrophenyl) anthranilic acid ("NPAA") (compound of formula (I) wherein $R_1$ is H, $R_2$ is $NO_2$, $R_4$ is H, and X is C) (see, "The Merck Index", 10th ed., monograph no. 7152);

Tolfenamic acid (compound of formula (I) where $R_1$ is H, $R_2$ is H, $R_3$ is cholorine, $R_4$ is $CH_3$ and X is C) (see, "The Merck Index", 10th ed., monograph no. 9341);

Flunixin (compound of formula (I) where $R_1$ is H, $R_2$ is H, $R_3$ is $CF_3$, $R_4$ is $CH_3$, and X is N) (see, "The Merck Index", 10th ed., monograph no. 4048); and, Etofenamate (compound of formula (I) where $R_1$ is H, $R_2$ is —$R_3$ is $CF_a$, $R_4$ is H, X is C, and $R_6$ is $COOCH_2$ ($CH_2$ $OCH_2$ $CH_2$ OH)) (see, "The Merck Index" 10th ed., monograph no. 3824).

The GABAergic compounds of the invention are available commercially (from, for example, Sigma Chemical (St. Louis, Mo.) and Aldrich Chemical (Milwaukee, Wis.), or may readily be prepared by those of ordinary skill in the art.

Effects Of Fenamates As GABAergic compounds

The compounds described above exert different GABAergic activity with respect to $GABA_A$ receptors dependent, principally, on factors such as GABA concentration, as well as concentration and conformation of the fenamate molecules. In this context, "GABAergic activity" is determined as a function of the response of $GABA_A$ receptors to GABA and the GABAergic compound, which response is expressed in terms of the electrical current ($I_G$) produced at the membrane of cells contacted with a GABAergic compound. As indicated by the $I_G$ measured in the presence of GABA and a given GABAergic compound of the invention, the agent may potentiate or inhibit the response of $GABA_A$ receptors to GABA. Generally, potentiation or inhibition of $GABA_A$ receptors responses to GABA appears as an increase, or a decrease, of membrane current relative to the $I_G$ which would be expected to be produced in response to GABA alone. For purposes of this disclosure, the amount of GABAergic agent which will achieve modulation of the responses to GABA will be considered a "potentiatory or inhibitory effective amount" of the GABAergic agent.

To varying degrees, the GABAergic compounds of the invention potentiate $GABA_A$ responses to low concentrations of GABA and inhibit $GABA_A$ responses to high concentrations of GABA. The potentiation response is particularly surprising for two reasons. First, to date, NSAIDs and other anti-inflammatory agents (e.g., quinolones) have only been shown to inhibit ion channel responses to ligands, including inhibition of $GABA_A$ receptor responses to GABA. Second, inhibition of GABA responses has been observed even at micromolar observed concentrations of the NSAID's or other compounds, (see, e.g., White, et al., *Mol. Pharmacol.*, 37:720–724, 1990). Thus, the potentiation of $GABA_A$ responses in particular by the GABAergic compounds of the invention was unexpected.

Increases in the concentration of the GABAergic compound in the presence of stable concentrations of GABA generally produces stronger potentiation or inhibition of $GABA_A$ receptor responses, depending on the potency of the GABAergic compound and the concentrations of GABA in contact with the receptor. Among the GABAergic compounds of the invention, their relative potency and activity (i.e., potentiation or inhibition) appears in part to be a function of the conformation of the molecule. Specifically, molecules constrained by steric hindrance to assume and retain non-planar conformation tend to potentiate $GABA_A$ responses to GABA. For example, molecules which have relatively bulky groups ortho to Y in formula (I) (e.g., mefenamic and meclofenamic acids) are relatively strong potentiating GABAergic compounds compared to niflumic acid, where X in formula (I) is nitrogen. In this regard, the presence of a carbon-based group at $R_2$ will be expected to generally enhance the potency of the GABAergic compound as will, to varying degrees, an increase in the hydrophobicity of the molecule.

Methods For Use of Fenamates As GABAergic compounds.

As noted above, fenamates have not been widely used as anti-inflammatory agents in the United States because of adverse gastrointestinal side effects. However, experience with clinical usage of these NSAIDs in Europe and Japan provides guidance regarding toxicity and dosage levels at which the fenamates can be expected to be active. Thus, in addition to their known antiinflammatory activity, the GABAergic compounds of the invention have value as pharmacological agents to treat disorders associated with hyporesponsiveness to GABA by $GABA_A$ receptors. Such compounds will also be useful in vitro to, for example, further characterize the activity and structure of $GABA_A$ receptors.

To this end, pharmaceutically acceptable compositions of the GABAergic compounds of the invention may be administered to a mammal (preferably, a human) in need of $GABA_A$ receptor response potentiation or inhibition in dosages sufficient to achieve peak plasma concentrations of about 4–40 µM. Generally, these concentrations will be achieved in vivo at dosages of 0.1 to 100 mg/kg$^{-1}$, body weight, preferably 20–30 mg/kg$^{-1}$, although skilled physicians will readily be able to adjust these dosages to achieve specific therapeutic ends.

It will be appreciated by those of skill in the art that in vivo use of the GABAergic compounds of the invention to modulate $GABA_A$ receptor responses in brain tissue will depend on the ability of such compounds to cross the blood/brain barrier. That ability may, however, be confirmed by administration of individual compounds in a suitable animal model, such as the murine model. Detection of the GABAergic compounds in the brain tissue may be made by means known to those of skill in the art.

For example, determination of whether a particular GABAergic agent of the invention will cross the blood/brain barrier can be made by one of ordinary skill in the art without undue experimentation by labelling the GABAergic agent with a label detectable in vivo, such as a radioisotope or paramagnetic isotope, and administering the detectably labelled agent to suitable individuals of an animal model for in vivo imaging of any such agent in the animal's brain tissue. An important factor in selecting a radioisotope for in vivo imaging is that the half-life of the radioisotope be long enough so that it is still detectable at the time of maximum uptake by the target, but short enough so that deleterious radiation with respect to the host is minimized. Suitable radioisotopes include $^{125}$I, $^{99m}$Tc, $^{111}$In, $^{97}$Ru, $^{67}$Ga, $^{68}$Ga, $^{72}$As, $^{89}$Zr, $^{90}$Y, and $^{201}$Ti. Of these, a preferred radioisotope for in vivo use is reduced [$^{99m}$Tc] pertechenetate for its relatively low toxicity in mammals. However, for any in vitro use, $^{125}$Iodide ($^{125}$I) would be preferred for ease of detection.

The GABAergic agents of the invention may also be labelled with a paramagnetic isotope for purposes of in vivo detection as in magnetic resonance imaging (MRI) or electron spin resonance (ESR). In general, any conventional method for visualizing detectable labels in vivo can be utilized. Usually gamma and positron emitting radioisotopes are used for camera imaging and paramagnetic isotopes for MRI. Elements which are particularly useful in such techniques also include $^{157}$Gd, $^{55}$Mn, $^{162}$Dy, $^{52}$Cr and $^{56}$Fe.

Preparation Of Pharmaceutically Acceptable GABAergic Compositions.

Pharmaceutically acceptable compositions including the GABAergic compounds of the invention, as well as salts and esters thereof, may be prepared as follows:

The pharmaceutically acceptable base salts of compounds of the formula (I) are those formed from bases which form non-toxic base salts. These particular non-toxic base salts include, but are not limited to sodium, potassium, calcium, and magnesium. These salts can easily be prepared by treating the acidic compounds of the formula (I) with an aqueous solution of the desired cation, and then evaporating the resulting solution to dryness, preferably while being placed under reduced pressure.

Alternatively, pharmaceutically acceptable base salts may also be prepared by mixing lower alkanoic solutions of the acidic compounds and the desired alkali metal alkoxide together, and then evaporating the resulting solution to dryness in the same manner as described above. In either case, stoichiometric quantities of reagents are preferably employed in order to ensure complete reaction and maximum yield of the desired pharmaceutically acceptable base salts.

As used herein, the term "in vivo hydrolyzable ester" refers to esters which are hydrolyzable under physiological conditions. Such esters are generally themselves inactive or low in activity, but are converted in vivo into active compounds of formula (I). Hydrolysis occurs in vivo uncatalytically or catalytically with an enzyme such as an esterase. Therefore, the esters are considered pro-drugs of the GABAergic compounds of the invention. The pro-drugs should have favorable properties, such as enhancement of absorption (particularly by enteral routes), water solubility, and lower toxicity.

Examples of such compounds are esters such as methyl, ethyl, phenyl, N,N-dimethylaminoethyl, acyl derivatives such as benzoyl, p-N,N-dimethylamino benzoyl, N,N-dimethylaminoglycyl, and peptide derivatives such as δ-glutamyl, glycyl. Additional preferred esters include acetoxymethyl, pivaloyloxymethyl, 1-(ethoxycarbonyloxy) ethyl, 3-phthalidyl, δ-butyrolacton-4-yl and 5-methyl-2-oxo-1,3-dioxol-4-yl-methyl esters. The preparation and activity of the latter groups of esters are well-documented in the penicillin and cephalosporin art.

After administration, the in vivo hydrolyzable esters of the compounds of formula (I) quickly break down in vivo at physiological pH to liberate the parent acidic compound of formula (I).

This invention is readily carried out. The compounds of this invention can be administered by either enteral or parental routes of administration, although intraarterial injection is the preferred route for in vivo introduction of the compounds into brain tissue.

For introduction of the compounds into peripheral target tissues, where gastrointestinal absorption permits, enteral administration is preferred for reasons of patient convenience and comfort, and can be carried out in either single or multiple dosages. The GABAergic compositions of the invention may be administered in combination with pharmaceutically acceptable carriers in a variety of dosage forms. For example, capsules, lozenges, hard candies, powders, sprays, aqueous suspension, elixirs, syrups, and the like may be formulated with various pharmaceutically-acceptable inert carriers. Such carriers include solid diluents or fillers, sterile aqueous media and various non-toxic organic solvents. In general, the GABAergic compounds of the invention will be included in oral dosage forms at concentration levels ranging from about 0.5% to about 90% by weight of the total composition, in amounts which are sufficient to provide the desired unit dosage.

Tablets may contain various excipients such as sodium citrate, calcium carbonate and calcium phosphate, along with various disintegrants such as starch (preferably potato or tapioca starch), alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

For parenteral use, the GABAergic compounds of the invention may be formulated by means known in the art using suitable dispersing or wetting agents and suspending agents. A sterile injectable formulation can also be a solution of suspension in a non-toxic parenterally acceptable diluent or solvent, for example, as a solution in 1,3-butandiol. Among the acceptable vehicles and solvents are water, Ringer's solution and isotonic NaCl solution, fixed oils (including synthetic mono-or di-glycerides), fatty acids (such as oleic acids), and mixtures thereof.

The GABAergic compounds of the invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, pharmaceutically acceptable and metabolizable lipid capable of forming liposomes can be used (see, for example, *Methods in Cell Biology* (Prescott, ed.; Academic: New York, Vol. XIV, 1976). Compositions prepared in liposome form can contain stabilizers, preservatives, excipients, and the like in addition to the agent. The preferred lipids are the phospholipids and the phosphatidyl cholines (lecithins), both natural and synthetic.

Additional pharmaceutical methods may be employed to control the duration of pharmacological action. Controlled release preparations may be achieved by the use of polymers to complex or adsorb the present active compounds. The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release.

Another possible method to control the duration of action by controlled release preparations is to incorporate the active compound into particles of a polymeric material such as polyesters, polyamino acids, hydrogels, poly (lactic acid) or ethylene vinylacetate copolymers. Alternatively, instead of incorporating the active compounds into these polymeric particles, it is possible to entrap the active compounds in microcapsules prepared, for example, by coacervation techniques or by interfacial polymerization using, for example, hydroxymethylcellulose or gelatin-microcapsules and poly (methylmethacrylate) microcapsules, or in colloidal drug delivery systems, for example, liposomes, albumin microspheres, microemulsions, nanoparticles, and nanocapsules or in macroemulsions. Techniques for preparing such controlled release formulation are known to those of skill in the art and described, for example, in *Remington's Pharmaceutical Science* (A. Oslo, Ed.; 17th ed.; Mack: Easton, Pa.), 1985.

The invention having been fully described, aspects of it are illustrated by the following examples. However, these examples do not limit the invention, which is defined by the appended claims.

EXAMPLE I

RNA EXTRACTION AND EXPRESSION OF GABA$_A$ RECEPTORS IN *Xenopus Laevis* OOCYTES Poly(A)$^+$ RNA was isolated from rat cerebral cortex either using the phenol/chloroform procedure known in the art (see, e.g., Woodward et al., *Mol. Pharmacol.*, 42:165–173, 1992), or using the well-known guanidinium thiocyanate/phenol/chloroform variant (Chomczynski, et al., *Anal. Biochem.* 162:156–159, 1987). For this particular study, three separate RNA preparations were used. Follicle-enclosed Xenopus oocytes (at stages V and VI of development) were microinjected with 50–100 ng of poly(A)$^+$ RNA (injection volume 50–100 nl). Oocytes were stored in Barth's medium containing (in mM) NaCl, 88; KCl 1; CaCl$_2$ 0.41; CA(NO$_3$), 2.4; HEPES, 5; pH adjusted to 7.4 with NaOH, usually with 0.1 mg/ml$^{-1}$ gentamycin, and were enzymatically defolliculated approximately 48 hrs after injection by incubating the cells for 0.5–1 hours in 0.5 mg ml$^{-1}$ Sigma type I collagenase (200 units ml$^{-1}$).

EXAMPLE II

PROTOCOL FOR MEASURING RECEPTOR RESPONSES (IGg)

Electrical recordings of the responses of the GABA$_A$ receptors of Example I to the compounds of the invention and GABA were made in frog Ringer solution containing (in mM) NaCl, 115; KCl, 2; CaCl$_2$, 1.8; HEPES, 5; pH adjusted to 7.0 with NaOH, using a two electrode voltage clamp. The holding potential for all recordings was −70 mV. In the data reported in the following examples, membrane current responses mediated by rat cerebral cortex GABA$_A$ receptors expressed in oocytes (see Example I) are denoted "$I_{G-Acx}$". Unless otherwise stated in the following examples, drugs were applied to oocytes by bath perfusion. At concentrations between 50–100 µM many of the NSAIDs caused slight (<0.1 pH unit) acidification of Ringer, and pH of solutions was therefore re-adjusted to 7.0 with NaOH to exclude any possibility of pH artifacts. The dicarboxylic acid, IDBA, lowered pH by between 0.1–0.15 pH unit.

EC$_{50}$ values and slope factors (pseudo-Hill coefficients) of concentration-response curves were calculated using a non-linear least squares curve-fitting program, based on a four parameter logistic equation well-known in the art (see, e.g., DeLean, et al., *Am. J. Physiol.* 235:E97-E102, 1978). IC$_{50}$ values were determined by simple regression.

EXAMPLE III

PREPARATION OF TEST COMPOUNDS

For the majority of the experiments described in the following examples, drugs were made up each day as fresh concentrated (1–100 mM) stocks in dimethylsulfoxide (DMSO) or water. In some cases stocks were stored for up to 48 hours, either at 4° C. or frozen at −20° C.; activity of these stocks did not appear to be appreciably different from freshly prepared solutions. Fenamate stocks were all in DMSO, except meclofenamic acid, which for some experiments was made up in water (at 100 mM, solutions were slightly cloudy). The NSAIDs diflunisal, fenoprofen, flurbiprofen, ibuprofen, indomethacin, ketoprofen, phenylbutazone, piroxicam, and sulindac, together with aniline, IDBA, NPAA, and TAA were also made up in DMSO. At concentrations up to 100 μM, none of these compounds showed clear signs of saturation in Ringer solutions. DMSO (≦0.2%) had no detectable effects on $I_{G-Actx}$. Acetylsalicylic acid (aspirin), diclofenac, naproxen, salicylic acid and tolmedin, together with anthranilic acid were made up in water, some stocks required gentle warming.

EXAMPLE IV

POTENTIATION OF $I_{G-Actx}$ BY THE GABAergic COMPOUNDS OF THE INVENTION

Test compounds were initially assayed on $I_{G-Actx}$ elicited in expressed $GABA_A$ receptors by 10 μM GABA, a response that constitutes <10% of maximum. Because experiments were ostensibly designed to gauge potency of inhibitory effects, it was surprising when each of the four compounds assayed in this study caused potentiation of the current. Relative effects of the different compounds were initially gauged by comparing levels of potentiation induced by fixed concentrations of drug (see FIG. 1A and Table 1 below). FIG. 1A shows (at the arrows) small, apparent outward currents associated with membrane conductance (for flufenamic and meclofenamic acid) that took 5–10 minutes to wash out. Control responses are shown at the dashed lines and inward currents are shown by downward deflections.

During these studies it also became clear that, in some oocytes, mefenamic acid and meclofenamate (10–100 μM) were themselves able to elicit membrane current responses through activation of the phosphoinositide/$Ca^{2+}$ pathway. For the most part, the oocytes tested failed to respond directly to fenamates.

TABLE 1

| FACILITATION OF $I_{G-Actx}$ BY NSAIDs[a] | | |
|---|---|---|
| | Potentiation at 10 μM (%) | Potentiation at 100 μM (%) |
| Fenamates. | | |
| Flufenamic acid | 156 ± 42 (6)[b] | ND[c] |
| Meclofenamate | 183 ± 40 (5) | ND |
| Mefenamic acid | 268 ± 71 (6) | ND |
| Niflumic acid | 28 ± 8 (5) | ND |
| Acetic acid. | | |
| Diclofenac | — (3)[d] | — (3) |
| Indomethacin | — (4) | 15 ± 10 (3) |
| Sulindac | 21 ± 7 (3) | 123 ± 19 (4) |
| Tolmetin | | — (3) |
| Propionic acids. | | |
| Fenoprofen | — (3) | 27 ± 6 (4) |
| Flurbiprofen | — (3) | −7 ± 4 (3)[e] |
| Ibuprofen | — (3) | 16 ± 5 (4) |
| Ketoprofen | — (3) | — (3) |
| Naproxen | | 11 ± 3 (3) |

TABLE 1-continued

| FACILITATION OF $I_{G-Actx}$ BY NSAIDs[a] | | |
|---|---|---|
| | Potentiation at 10 μM (%) | Potentiation at 100 μM (%) |
| Salicylates. | | |
| Acetylsalicylic acid | — (3) | — (3) |
| Diflunisal | 155 ± 24 (4) | 191 ± 29 (4) |
| Pyrazoles. | | |
| Phenylbutazone | — (3) | −9 ± 2 (3) |
| Oxicams. | | |
| Piroxicam | — (3) | 14 ± 9 (3) |

[a]Levels of potentiation were assayed on $I_{G-Actx}$ elicited by 10 μM GABA (<10% of maximum current) using oocytes from the same frog.
[b]Data are mean ± S.D., with number of experiments given in parentheses.
[c]ND not determined. Effects of 100 μM fenamates were not measured using oocytes from this particular frog.
[d]—, no appreciable effect (<5% change from control).
[e]Negative numbers indicate inhibition of current.

Levels of potentiation of $I_{G-Actx}$ appeared to equilibrate rapidly upon application of fenamates (Table 1). For example, extended (5–15 min) pre-incubations in 0.5–10 μM mefenamic acid resulted in only marginally higher levels of facilitation compared to when the fenamate was co-applied with GABA. Concentrations necessary to induce threshold levels of potentiation (i.e., potentiatory effective amounts) were 0.1–0.3 μM for mefenamic and meclofenamic acids, 0.3–1 μM for flufenamic acid, and 1–10 μM for niflumic acid. $EC_{50}$ values for the facilitatory effects were: mefenamic acid, 5.2±1 μM; meclofenamic acid, 6.0±μM; flufenamic acid 8.8±1.2 μM; niflumic acid 10.5±4 μM (all data given as mean ±S.D., n=3–4). Slope values for the concentration dependence of the modulation ranged between 1.5 to 2.6.

Figure 2:
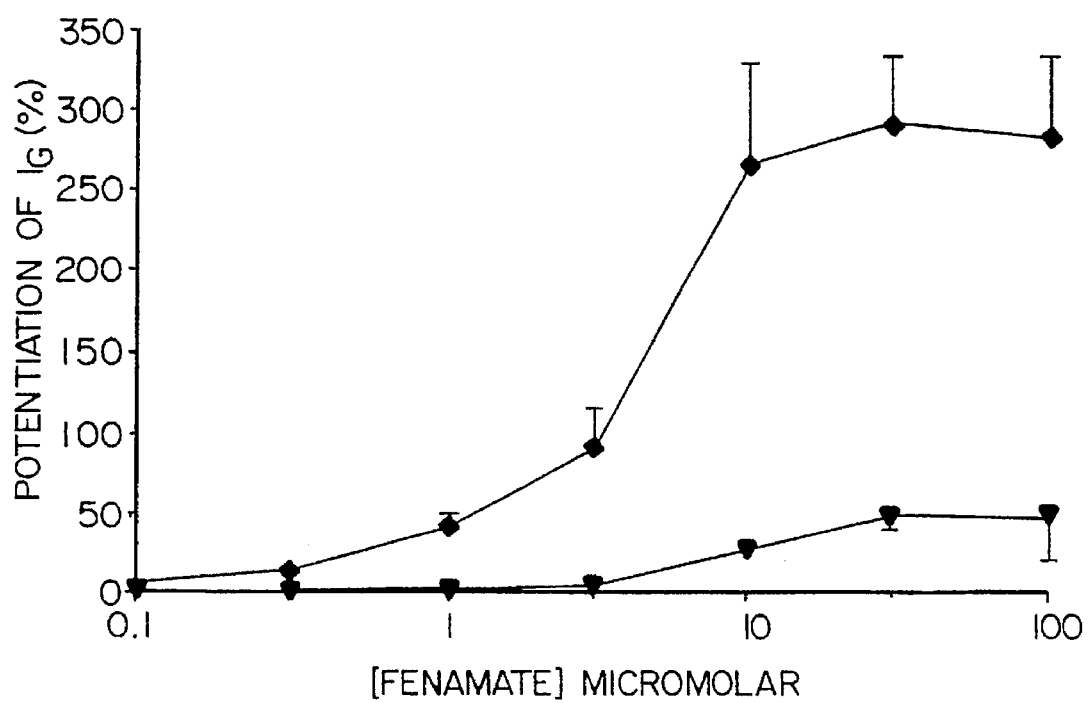
FIG. 2 demonstrates the concentration dependence of the $GABA_A$ potentiating capacity of mefenamic and niflumic acids. $EC_{50}$ values were calculated by curve fitting to individual curves.

Curves comparing effects of mefenamic and niflumic acids are shown in FIG. 2 (based on 1 minute pre-incubation of the compounds and 5–40 minute wash intervals, depending on the concentration of compounds applied). These experiments showed that there were clear differences in efficacy between the four fenamates tested, most strikingly between mefenamic acid, where maximum levels of potentiation were ≈300%, and niflumic acid, where maximum potentiation was <50%. Meclofenamic and flufenamic acids had intermediate efficacies.

Figure 3A:
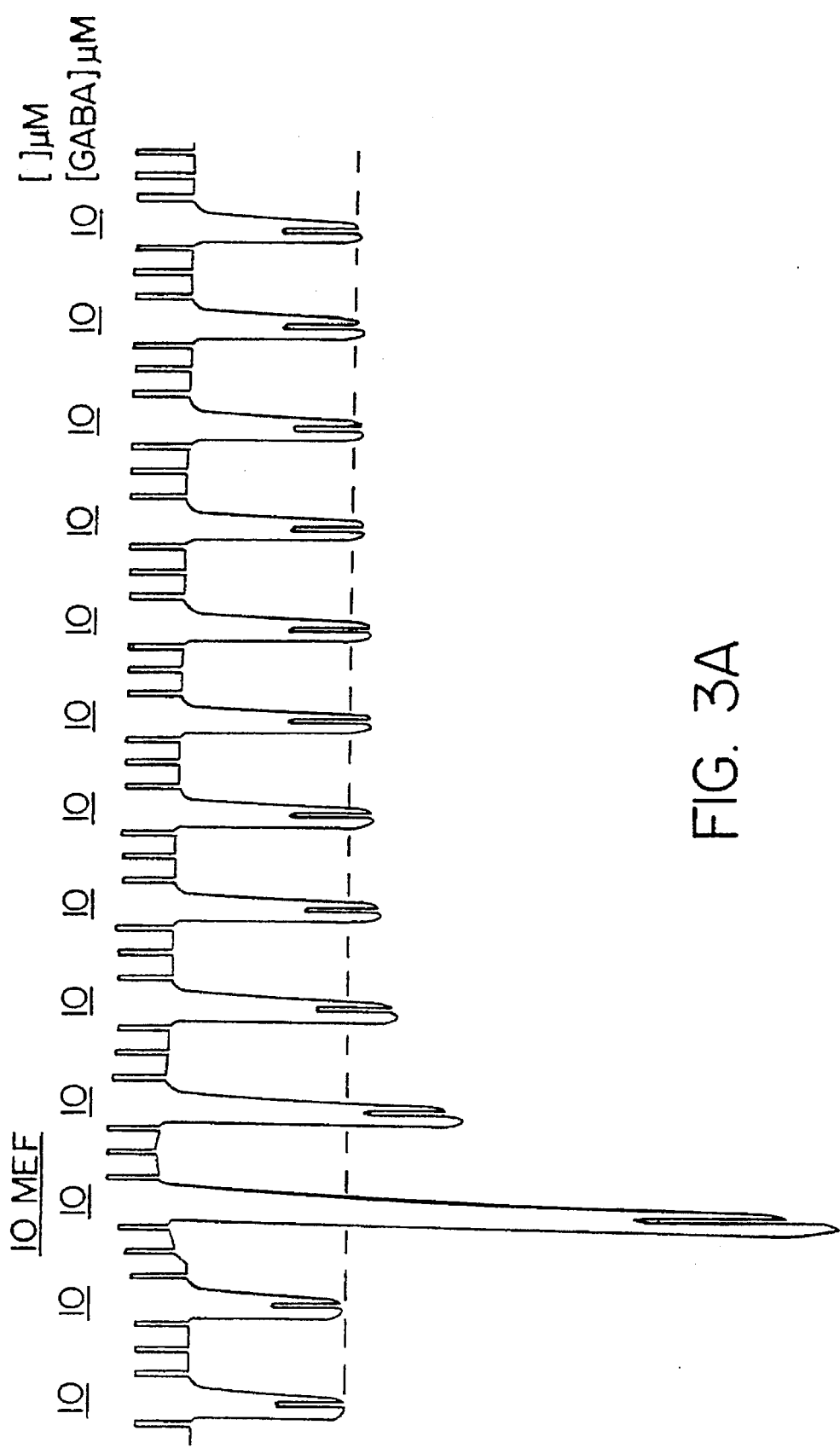
FIG. 3 (A–B) depicts typical time courses for potentiation by mefenamic acid. Oocytes were repeatedly exposed to GABA for 30 seconds at two minute intervals. 10 μM mefenamic acid amplified the current response of $GABA_A$ receptors by 325%, an effect which was reduced 90% by a 1 minute wash.
Figure 3B:
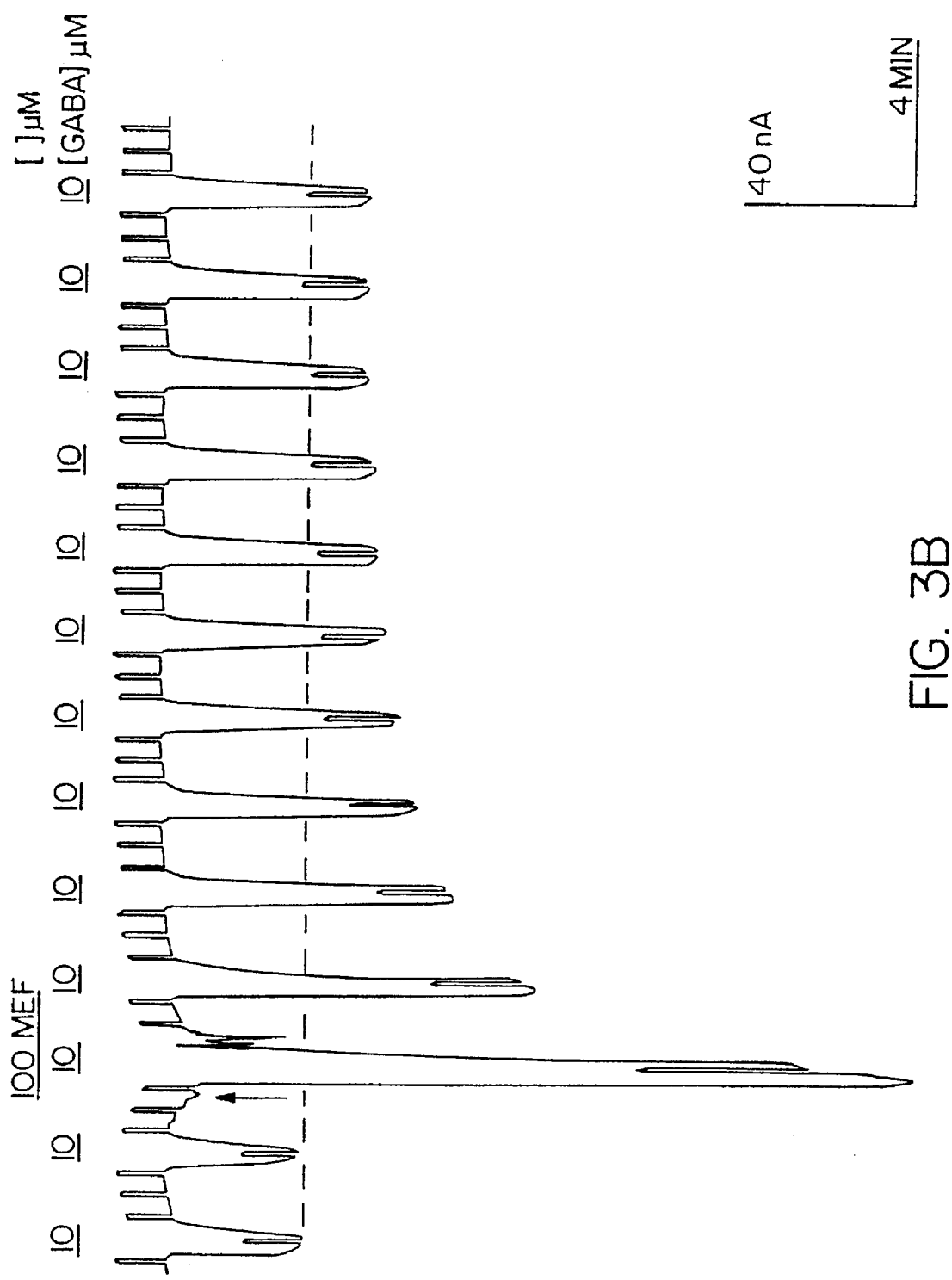

Recovery from potentiation followed similar time courses for all four fenamates. Facilitatory effects of 0.3–1 μM mefenamic acid and meclofenamate were essentially undetectable after 3–10 minute wash. Facilitation induced by fenamates applied at 10 μM was reduced >80% after only a 1 minute wash, but there often appeared to be small residual effects even after 20 minutes. The time course for washing out the GABA receptor modulation induced by 10 μM mefenamic acid is illustrated in FIG. 3A. Following applications of 100 μM fenamate, a substantial component of the effect again washed out rapidly, but these experiments clearly revealed a long lasting residual level of potentiation (20–40%), which was still detectable even after a 60 minute wash and numerous 30 second applications of GABA (FIG. 3B).

EXAMPLE V

INHIBITION OF $I_{G-Actx}$ BY THE GABAergic COMPOUNDS OF THE INVENTION

Figure 4A:
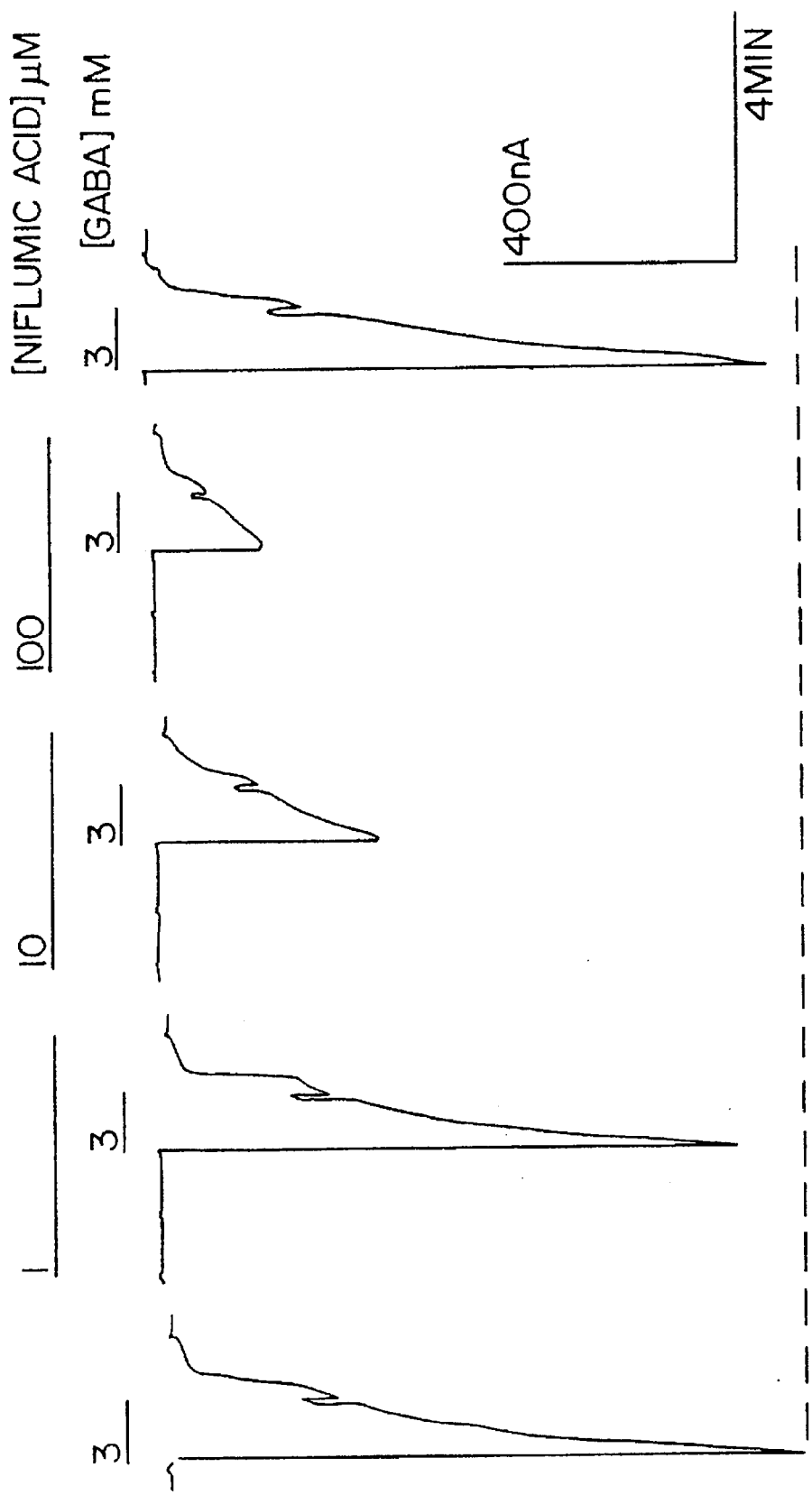
FIG. 4 (A–B) demonstrates the inhibitory capacity of the GABAergic compounds of the invention. Records were separated by 20 minute intervals. The final record is the control response following a 40 minute wash.
Figure 4B:
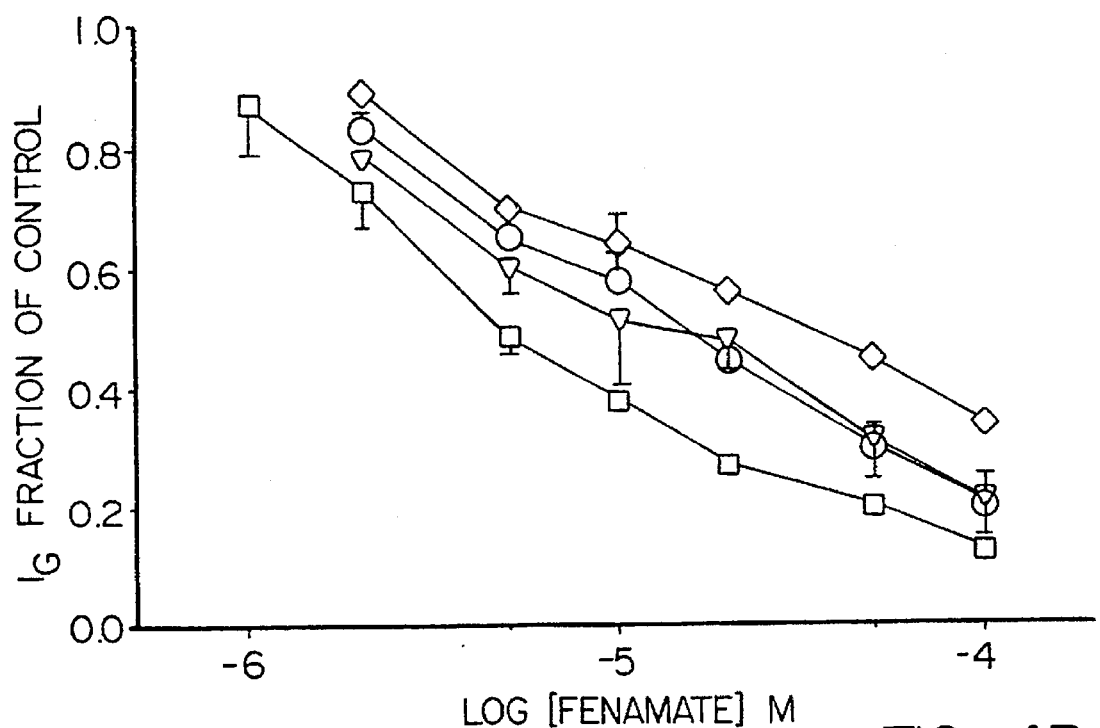

Assays on maximum responses (currents elicited by 3 mM GABA) showed that all four fenamates also had clear inhibitory effects on $I_{G-Actx}$. As shown in FIG. 4 and Table 2, $IC_{50}$ values were determined giving an apparent potency sequence: niflumic acid (1.0)>meclofenamate (0.5) ≧flufenamic acid (0.4) >mefenamic acid (0.2): (numbers in parentheses are the relative potency with respect to niflumic acid (with applications of GABA for one minute)). It should be noted, however, that concerns over solubility prohibited use of fenamates at concentrations much over 100 µM where inhibition was incomplete (≈70–90%). It therefore remains unclear whether the fenamates showed actual differences in inhibitory efficacy.

EXAMPLE VI

EFFECTS OF CONCENTRATION ON RESPONSE CURVES FOR $I_{G-Actx}$

Figure 5A:
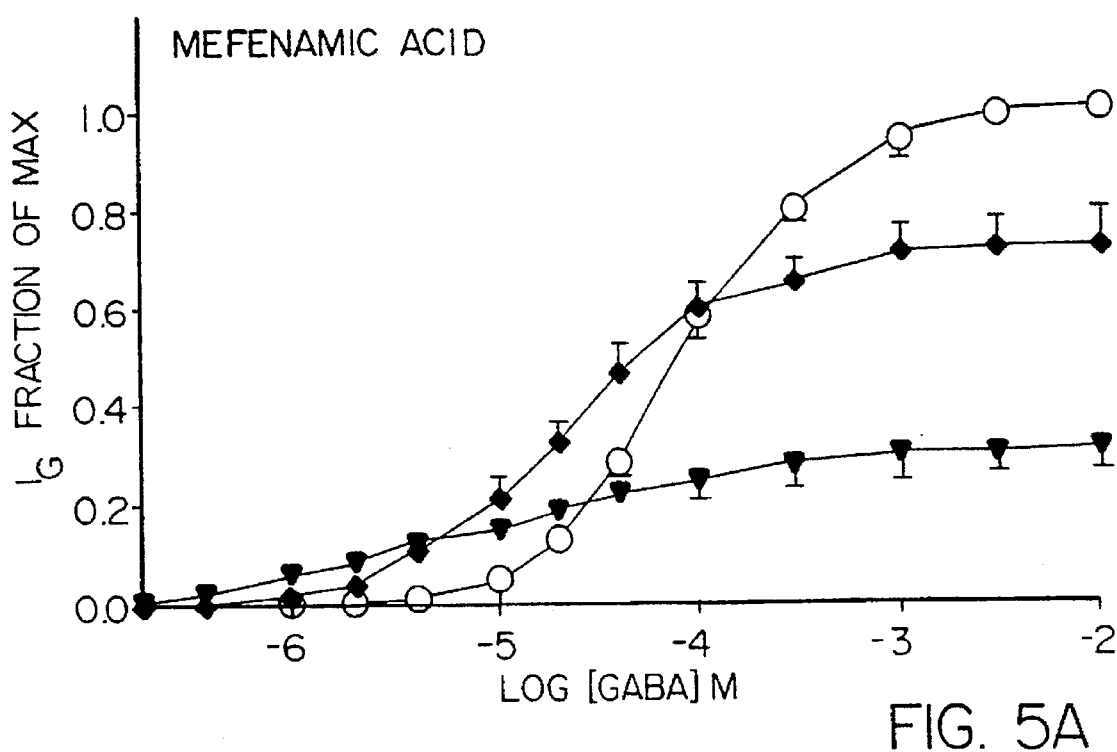
FIG. 5 (A–C) shows concentration response curves comparing the effects of mefenamic acid, flufenamic acid and niflumic acid on $I_{G-Actx}$. Data are the mean expressed as a fraction of maximum responses (i.e., the current elicited by 3 mM GABA).
Figure 5B:
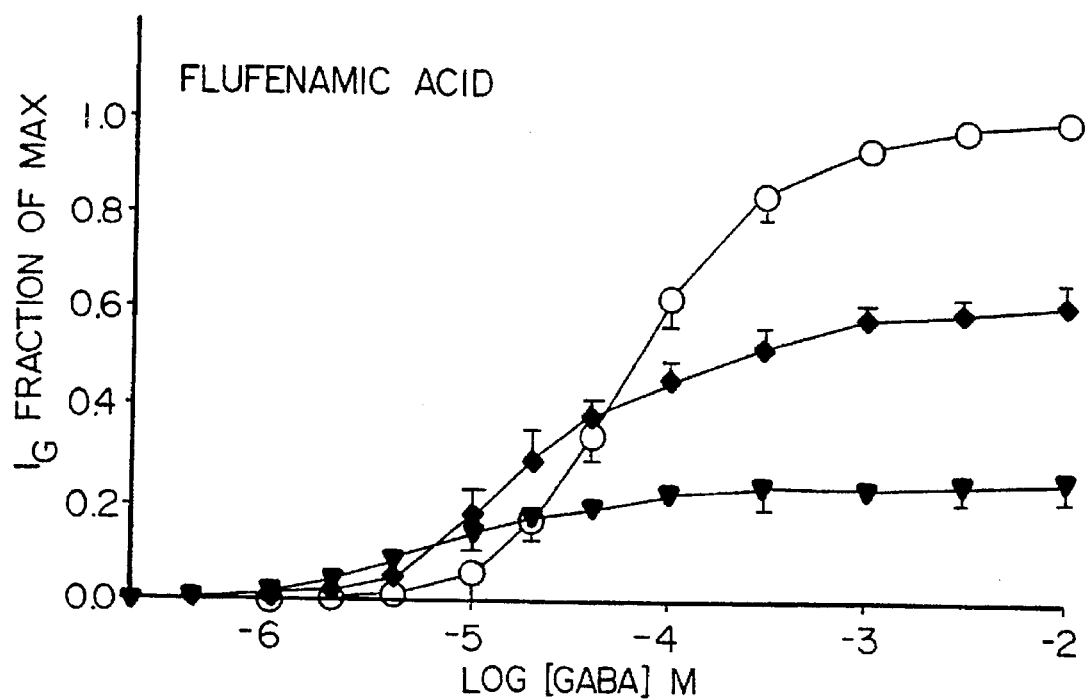
Figure 5C:
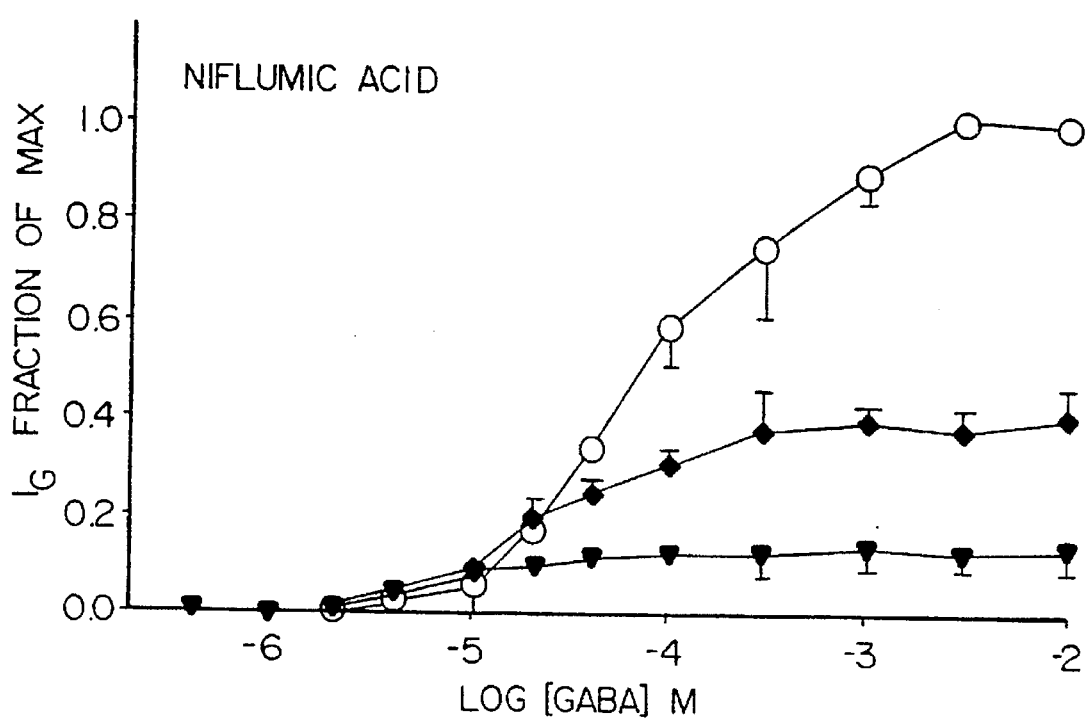

To characterize the dual action of fenamates on $I_{G-Actx}$ more fully effects were assayed over complete GABA concentration-response curves. As shown in FIG. 5A–C, these experiments confirmed that mefenamic acid had the highest efficacy in terms of facilitatory effects and also appeared to be the weakest inhibitor. Niflumic acid had the weakest facilitatory effects and was the strongest inhibitor while meclofenamic (not illustrated) and flufenamic acids had intermediate activities. Data in FIG. 5 are expressed as a fraction of maximum responses (current elicited by 3 mM GABA).

The $EC_{50}$ for $I_{G-Actx}$ was reduced from a control value of 81±10 µM to 63±4 µM by 1 µM mefenamic acid (not shown in FIG. 5), and to 23±4 mefenamic acid (n=4). At 1 µM, mefenamic acid shifted the concentration-response curve without reductions in slope or maximum response, whereas using 10 µM mefenamic acid the shift was accompanied by a 28±8% reduction in maximum current (n=4). Under these conditions the transition between net facilitatory and inhibitory effects occurred at approximately 100 µM GABA (FIG. 5A). In contrast, 10 µM niflumic acid caused no clear leftward shifts in concentration-response curves, reduced maximum responses by 54 ±1% (n=3), and had net inhibitory effects on all responses elicited by concentrations >20 µM GABA (FIG. 5B). At 100 µM, mefenamic acid caused further potentiation of currents elicited by low concentrations of GABA, reducing response threshold from ≈1 µM GABA, to as low as 50 nM.

However, at 100 µM, mefenamic acid had net inhibitory effects on currents diluted by GABA at concentrations >20 µM. Inhibition of $I_{G-Actx}$ by all the fenamates appeared to be largely or wholly unsurmountable. For example, increasing GABA concentrations from 3 to 30 mM caused little change in the level of inhibition induced by 10 or 100 µM niflumic acid.

EXAMPLE VII

COMPARISON OF $GABA_A$ RESPONSES IN THE PRESENCE OF OTHER NSAIDs

Figure 1B:
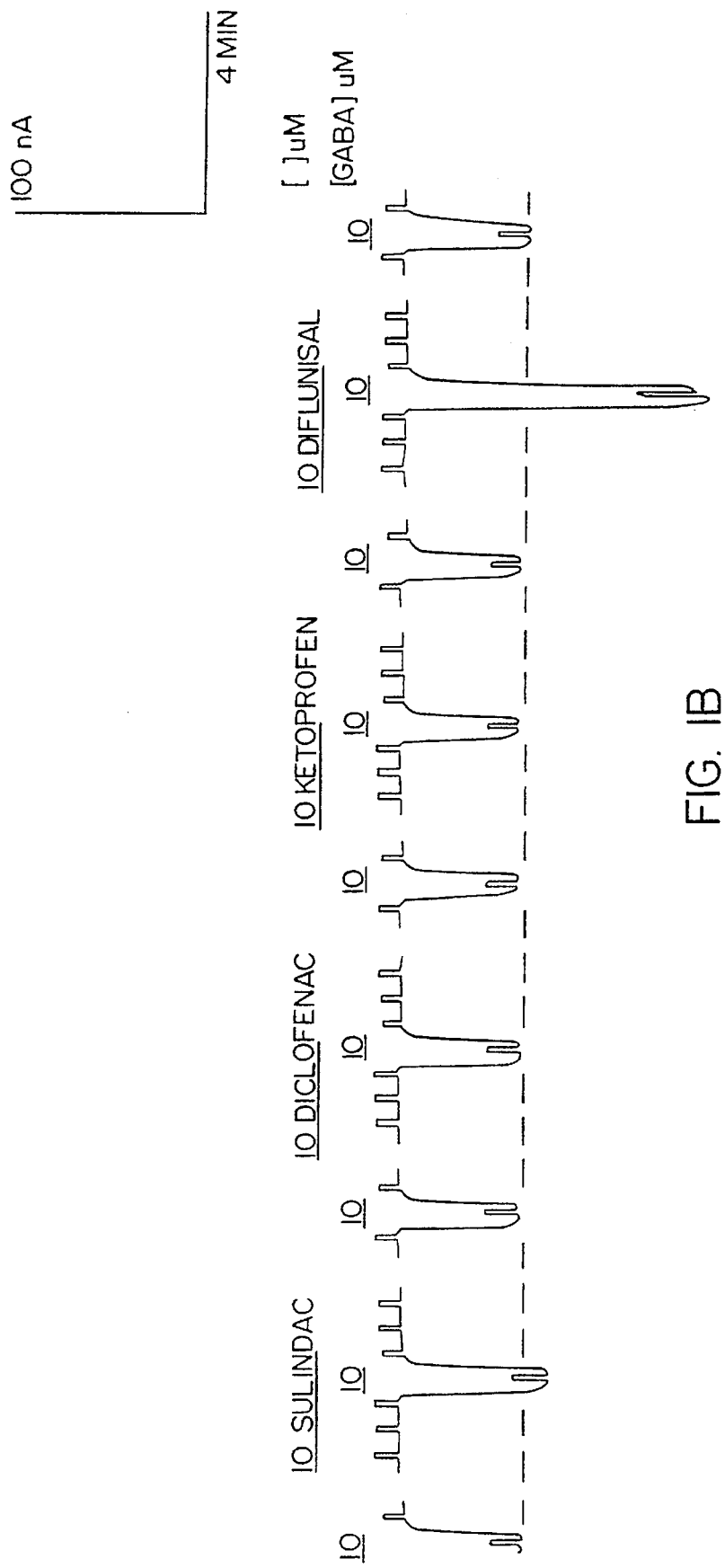

To confirm the uniqueness of the GABAergic effects of the compounds of the invention among NSAIDs with similar biological activity (i.e., prostaglandin synthesis inhibition) other NSAIDs were tested for potentiation of $I_{G-Actx}$ elicited by 10 µM GABA (see, FIG. 1B and Table 1). At concentrations ≦10 µM, only the acetic acid sulindac, and the salicylic acid diflunisal, had any appreciable effects. Actions of sulindac were relatively weak, similar to niflumic acid, whereas the effects of diflunisal were comparable with flufenamic and meclofenamic acids. When the NSAIDs were applied at 100 µM, fenoprofen also appeared to induce some weak potentiation, whilst indomethacin, ibuprofen, naproxen and piroxicam caused marginal increases, and flurbiprofen and phenylbutazone slight reductions in current.

The same NSAIDs were then assayed for inhibitory effects on maximum $I_{G-Actx}$ (See Table 2). Applied at 100 µM, only indomethacin and diflunisal caused any pronounced inhibition. $IC_{50}$ values were calculated for these drugs and showed that diflunisal appeared to be slightly less potent than flufenamic and meclofenamic acids, whereas indomethacin had roughly half the potency of mefenamic acid. Diclofenac, sulindac, flurbiprofen and phenylbutazone had weak or marginal effects which did not seem to warrant calculation of $IC_{50}$.

TABLE 2

| INHIBITION OF $I_{G-Actx}$ BY NSAIDs[a] | | |
|---|---|---|
|  | Potentiation at 10 µM (%) | Potentiation at 100 µM (%) |
| Fenamates. | | |
| Flufenamic acid | 80 ± 3 (3)[b] | 16 ± 3 (3) |
| Meclofenamate | 79 ± 6 (3) | 14 ± 3 (3) |
| Mefenamic acid | 65 ± 5 (9) | 33 ± 5 (4) |
| Niflumic acid | 86 ± 3 (6) | 7 ± 1 (3) |
| Acetic acid. | | |
| Diclofenac | 27 – 10 (3) | ND[c] |
| Indomethacin | 58 – 1 (4) | 77 ± 8 (3) |
| Sulindac | 16 ± 4 (3) | ND |
| Tolmetin | — (3)[d] | ND |
| Propionic acids. | | |
| Fenoprofen | — (3) | ND |
| Flurbiprofen | 10 – 4 (3) | ND |
| Ibuprofen | — (3) | ND |
| Ketoprofen | — (3) | ND |
| Naproxen |  | ND |
| Salicylates. | | |
| Acetylsalicylic acid | — (3) | ND |
| Diflunisal | 71 ± 4 (5) | 21 ± 2 (3) |
| Pyrazoles. | | |
| Phenylbutazone | 21 – 4 (4) | ND |
| Oxicams. | | |
| Piroxicam | — (3) | ND |

[a]Levels of inhibition were assayed on $I_{G-Actx}$ elicited by 3 mM GABA maximum response.
[b]Data are mean ± S.D., wiht number of experiments given in parentheses.
[c]ND not determined.
[d]—, no appreciable effect (<5% change from control).

EXAMPLE VIII

Figure 6A:
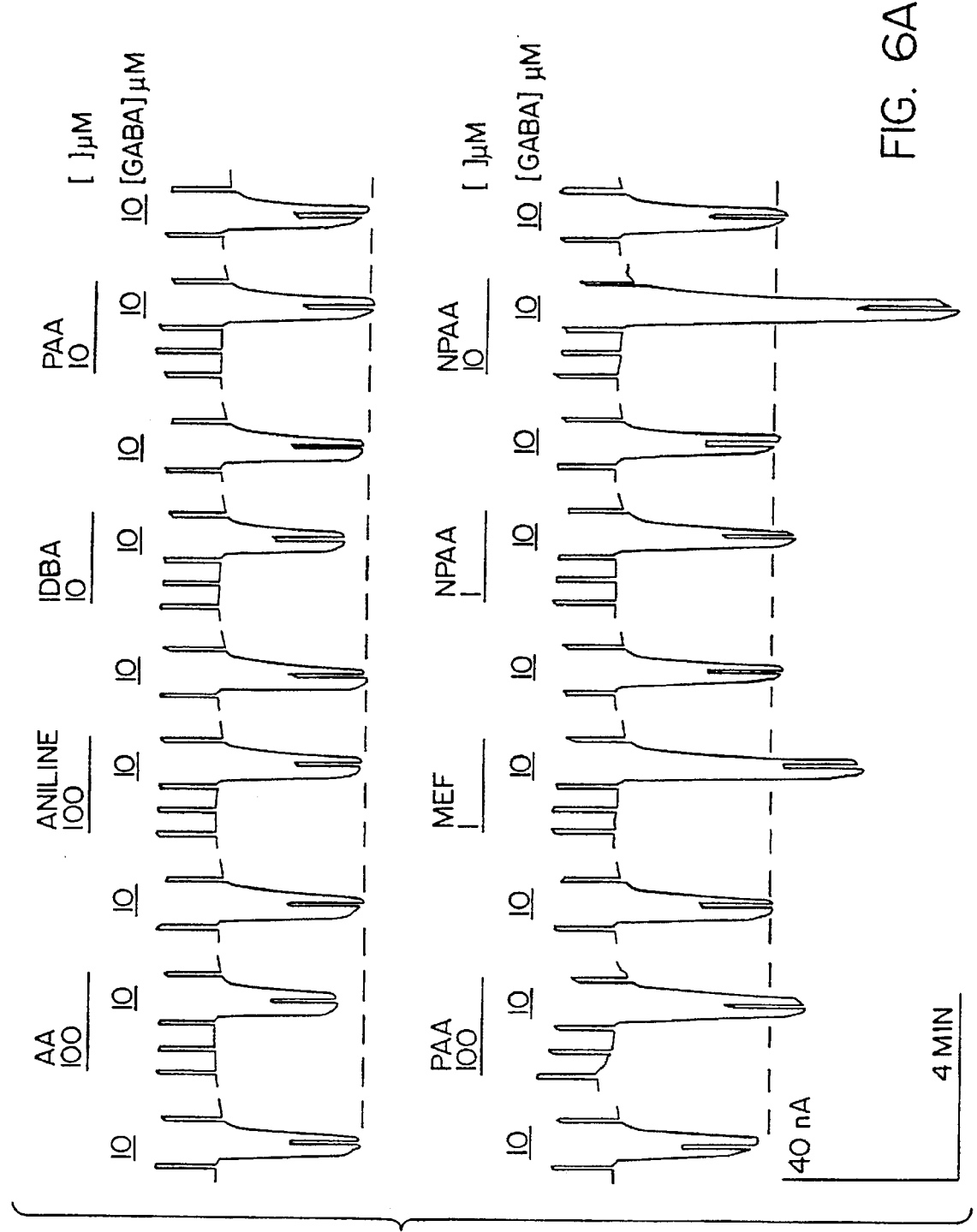
FIG. 6 (A–B) compares the potentiating ability of NSAIDs which are structurally related to the GABAergic compounds of the invention. Currents in A and B were recorded from two different oocytes and in the order given, with 2–15 minute intervals between records, depending on the level of potentiation. "AA" in the FIGURE refers to anthranilic acid.

IMPACT OF STRUCTURAL MODIFICATIONS OF THE GABAergic COMPOUNDS OF THE INVENTION To determine the effect of structure on the activity of the GABAergic compounds of the invention, the issue was addressed whether either ring structure alone, and without substituents, had modulatory effects on $GABA_A$ receptors. Again using $I_{G-Actx}$ elicited by 10 µM GABA, assays showed that neither aniline (1–100 µM) nor anthranilic acid potentiated the response. Indeed, the only appreciable effect was that 100 µM anthranilic acid reduced current by approximately 15% (FIG. 6A). Assays on maximum indicated aniline and anthranilic acid were similarly inactive as inhibitors. It was then investigated whether it was necessary to have any substituents on the phenyl ring for modulatory activity. Similar assays showed that 10 μM PAA was essentially inactive, and 100 μM PAA caused only weak (30–40%) potentiation (FIG. 6). Maximum $I_{G-Actx}$ was reduced 35–45% by 100 μM PAA.

Finally, the effects of three phenyl group substitutions were tested, to wit:

1. Introduction of a carboxyl group ortho to the imino linkage.

2. 2'-Iminodibenzoic acid (IDBA) appeared to be wholly inactive as a positive modulator of $I_{G-Actx}$. In fact, at concentrations ≥100 μM, IDBA had only inhibitory effects on currents elicited in the same oocyte (with 2–15 minute intervals between records) by 10 μM GABA (FIG. 6A).

2. Introduction of a nitro group meta to the imino linkage.

In contrast to IDBA, N-(3-nitrophenyl) anthranilic acid (NPAA) induced clear facilitation of 10 μM GABA responses (FIG. 6A), and, like the fenamates, also had inhibitory effects on currents elicited by high concentrations of GABA. For comparison, 100 μM NPAA reduced maximum $I_{G-Actx}$ by 60±11% (n=3). One potentially interesting property of the modulation induced by NPAA was that it washed out relatively rapidly, even when using high concentrations. For example, potentiation induced by 100 μM NPAA (350–400%) appeared to be completely washed out within <10 minutes whereas in the same cell residual effects of 100 μM mefenamic acid were still present after 60 minutes.

3. Removal of the meta methyl group of mefenamic acid.

N-(O-tolyl)anthranilic (TAA) acid had clear modulatory effects on currents elicited by 10 μM GABA, but was approximately ten times less potent than mefenamic acid (FIG. 6B). TAA also weakly inhibited maximum GABA responses, for instance, 100 μM TAA reduced currents by approximately 35%.

We claim:

1. A method for potentiating the response of mammalian $GABA_A$ receptors to GABA comprising contacting the $GABA_A$ receptors in the presence of GABA with at least a potentiatory amount of a GABAergic agent having the formula:

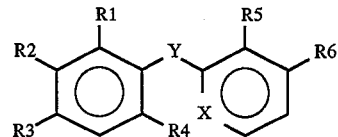

wherein X is C; Y is N or a direct bond; $R_1$ is $CH_3$; $R_2$ is $CH_3$; $R_3$ is H, halogen, $CH_3$ or $CF_3$; $R_4$ is H; $R_5$ is H, COOH; and, $R_6$ is H or COOH, with the provisos that if $R_5$ is H, then $R_6$ will always be COOH and, if $R_6$ is H, then $R_5$ will always be COOH or a pharmaceutically acceptable salt or hydrolyzable ester thereof.

2. The method according to claim 1, wherein the halogen of $R_3$ of the GABAergic agent is fluorine or chlorine.

3. The method according to claim 1, wherein the GABAergic agent is a pharmaceutically acceptable salt of the formula of claim 1 and the $GABA_A$ receptors are contacted with said pharmaceutically acceptable salt.

4. The method according to claim 1, wherein the GABAergic agent is a hydrolyzable ester of the formula of claim 1 and the $GABA_A$ receptors are contacted with said hydrolyzable ester.

5. The method according to claim 1, wherein the GABAergic agent is contained in a pharmaceutically acceptable composition and the $GABA_A$ receptors are contacted with said pharmaceutically acceptable composition.

6. The method according to claim 5 wherein the $GABA_A$ receptors are contacted in vivo in a mammal in need of potentiation of $GABA_A$ responses to GABA.

7. The method according to claim 6 wherein the mammal is a human.

* * * * *